United States Patent [19]

Overbye et al.

[11] Patent Number: 5,188,961
[45] Date of Patent: Feb. 23, 1993

[54] DNA ENCODING A STREPTOMYCES ENDOCHITINASE 56 SIGNAL PEPTIDE

[75] Inventors: Karen M. Overbye, Stoneham; Janice Pero, Lexington; Phillips W. Robbins, Beverly, all of Mass.

[73] Assignee: Omnigene, Inc., Cambridge, Mass.

[21] Appl. No.: 473,309

[22] Filed: Feb. 1, 1990

Related U.S. Application Data

[63] Continuation of Ser. No. 24,002, Mar. 10, 1987, abandoned.

[51] Int. Cl.$^5$ .................... C12N 15/74; C12N 15/52; C12N 1/21
[52] U.S. Cl. .................. 435/252.31; 435/69.1; 435/71.2; 435/169; 435/172.1; 435/172.3; 435/240.4; 435/252.3; 435/252.33; 435/252.34; 435/252.35; 435/320.1; 536/23.2; 536/23.7; 536/24.1; 935/6; 935/9; 935/14; 935/22; 935/29; 935/48
[58] Field of Search .............. 536/27; 435/69.1, 71.2, 435/91, 172.1, 172.3, 169, 320.1, 886, 252.3, 252.31, 252.33, 252.34, 252.35, 240.4; 935/6, 8, 9, 14, 22, 24, 29, 33, 39, 47, 48, 59, 60, 61, 66, 72, 75

[56] References Cited

U.S. PATENT DOCUMENTS 4,751,081 6/1988 Suslow et al. ............... 424/93 A

FOREIGN PATENT DOCUMENTS 0157351 10/1985 European Pat. Off. .
0171381 2/1986 European Pat. Off. .

OTHER PUBLICATIONS

Fishman et al., 1985, J. Bacteriol., vol. 161:199-206.
Trumbly et al., J. Biol. Chem., vol. 26, #9, (1985), pp. 5683-5690.
Ghrayeb et al., EMBO, vol. 3, #10, (1984), pp. 2437-2442.
Trimble et al., J. Biol. Chem., vol. 254, #19, (1979), pp. 9708-9711.
Fuchs et al., *Applied and Environ. Microbiol.*, 51(3):504-509 (1986).
Trimble et al., Methods in Enzymology, (1982), pp. 604, 1st paragraph.

*Primary Examiner*—Richard A. Schwartz
*Assistant Examiner*—Nancy T. Vogel
*Attorney, Agent, or Firm*—Fish & Richardson

[57] ABSTRACT

Engineered DNA encoding a pre-protein which comprises a Streptomyces chitinase signal sequence and a desired mature protein. Preferably, the signal sequence is from the *S. plicatus* endochitinase gene. The engineered DNA is included in a host organism causing the host to produce and secrete the mature protein. Where the mature protein is a chitinase, the invention is used in methods of controlling chitinase-sensitive pests.

15 Claims, 7 Drawing Sheets

| Met | Thr | Met | Ile | Thr | Asn | Ser | Ser | Ser | Val | Pro | Gly |
|-----|-----|-----|-----|-----|-----|-----|-----|-----|-----|-----|-----|
| ATG | ACC | ATG | ATT | ACG | AAT | TCG | AGC | TCG | GTA | CCC | GGG | pUC-18 | F1

| Asp | Pro | Ala | His | Met | Arg | Ile | Arg | His | Lys | Ala | Ala |
|-----|-----|-----|-----|-----|-----|-----|-----|-----|-----|-----|-----|
| GAT | CCG | GCG | CAC | ATG | CGT | ATC | AGA | CAC | AAA | GCC | GCG |

| Ala | Leu | Ala | Ala | Thr | Leu | Ala | Leu | Pro | Leu | Ala | Gly |
|-----|-----|-----|-----|-----|-----|-----|-----|-----|-----|-----|-----|
| GCA | CTC | GCA | GCG | ACC | CTG | GCG | CTT | CCC | CTC | GCC | GGC |

31

| Leu | Val | Gly | Leu | Ala | Ser | Pro | Ala | Gln | Ala | Ala | Thr |
|-----|-----|-----|-----|-----|-----|-----|-----|-----|-----|-----|-----|
| CTG | GTC | GGC | CTC | GCG | AGC | CCG | GCC | CAG | GCG | GCC | ACC |

| Ser | Ala | Thr | Ala | Thr | Phe | Gln | Lys | Thr | Ser | Asp | Trp |
|-----|-----|-----|-----|-----|-----|-----|-----|-----|-----|-----|-----|
| AGC | GCG | ACG | GCC | ACC | TTC | CAG | AAG | ACC | TCG | GAC | TGG |

FIG. 1a

TAGTTTTCCCTAGTCAGTCACAGGTTCAACCAC
TGGCCGCCACATTGGTCCAGACCTATTGACCTGTGGTCCAGACCTTTCTA
TTCTCGCCGCACTGCGGGCATGAGGCTCAGTCATGCCCTCGACAACATCC

| | | Met | Arg | Ile | Arg | His | Lys | Ala | Ala |
|---|---|-----|-----|-----|-----|-----|-----|-----|-----|
| CCATAAAAGGAGGCGCAC | | ATG | CGT | ATC | AGA | CAC | AAA | GCC | GCG |

| Ala | Leu | Ala | Ala | Thr | Leu | Ala | Leu | Pro | Leu | Ala | Gly |
|-----|-----|-----|-----|-----|-----|-----|-----|-----|-----|-----|-----|
| GCA | CTC | GCA | GCG | ACC | CTG | GCG | CTT | CCC | CTC | GCC | GGC |

| Leu | Val | Gly | Leu | Ala | Ser | Pro | Ala | Gln | Ala | Ala | Thr |
|-----|-----|-----|-----|-----|-----|-----|-----|-----|-----|-----|-----|
| CTG | GTC | GGC | CTC | GCG | AGC | CCG | GCC | CAG | GCG | GCC | ACC |

| Ser | Ala | Thr | Ala | Thr | Phe | Gln | Lys | Thr | Ser | Asp | Trp |
|-----|-----|-----|-----|-----|-----|-----|-----|-----|-----|-----|-----|
| AGC | GCG | ACG | GCC | ACC | TTC | CAG | AAG | ACC | TCG | GAC | TGG |

FIG. 1b

1. BamHI digestion
2. Bal31
3. BamHI linker
   Ligate into EcoRV of pBR322
4. Transform *E. coli* to amplify DNA.
   Screen and select plasmid pCT4
5. Take remainder of amplified DNA; digest with BamHI and XhoI
6. Clone into BamHI and SalI-cut pUC18
7. Screen in *E. coli* and select plasmid pCTF1

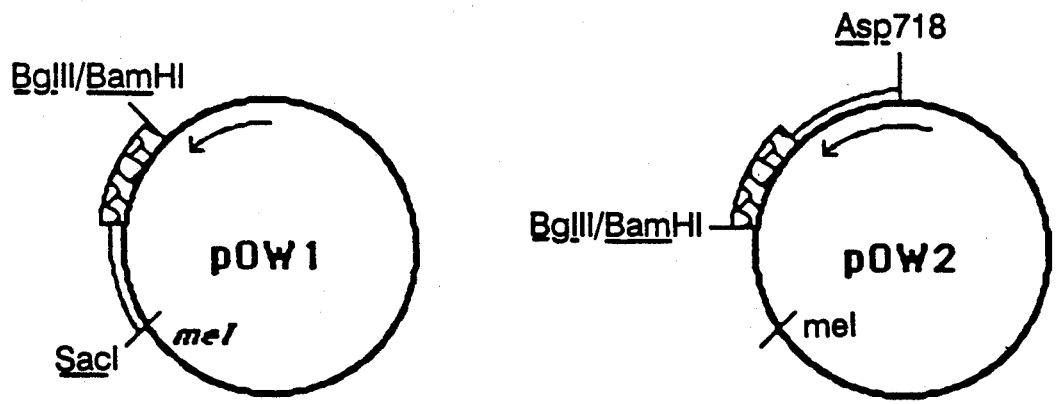
High-copy Streptom vectors - backbone pSEH (derivitive of pIJ702)
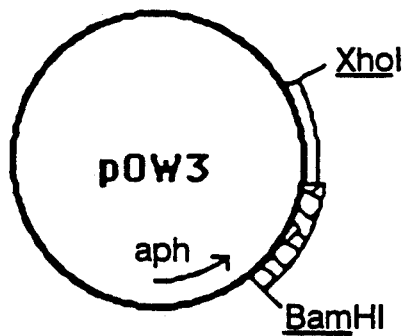
Low-copy Streptomyces vector - backbone pIJ61
 = Chitinase gene
FIG. 3 pCT4
1. Digest with BamHI and SacI
2. Isolate fragment with chitinase gene
3. Ligate fragment into BamHI- and SacI-cut pUC19, creating plasmid pCB5
pCH3
1. Digest with PstI
2. Isolate fragment with phoA gene
3. Ligate fragment into PstI-cut pUCB, creating pNH214
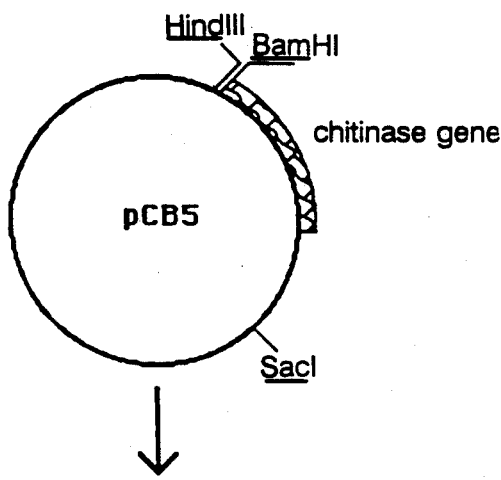
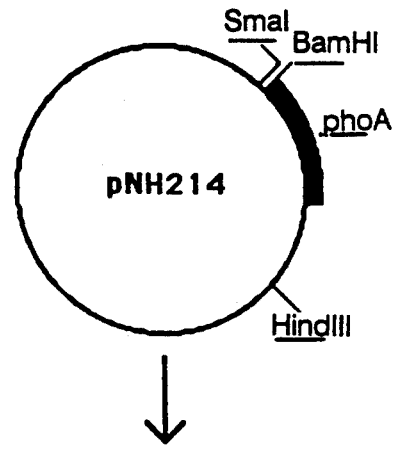
EaeI partial digest → Klenow
SmaI digest
Blunt-end ligate
Screen for phoA expression in E. coli
Isolate plasmid pPR5
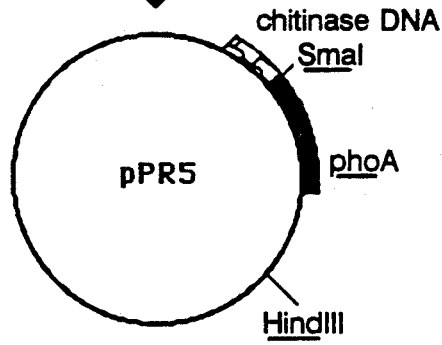
FIG. 4

```
        +29  +30  +31                              +32  +33  +34

Gln  Ala  Ala  Gly  Ser  Ala  Ala  Ala  Thr  Ser  Ala
        CAG  GCG  GCC  GGA  TCC  GCT  GCA  GCC  ACC  AGC  GCG
                       └────┘    └────────┘
signal                  BamHI       PstI                    structural gene
sequence
```

Region underlined contains the
15 base pair insert.

FIG. 6

DNA ENCODING A STREPTOMYCES ENDOCHITINASE 56 SIGNAL PEPTIDE

This is a continuation of co-pending application Ser. No. 07/024,00 filed on Mar. 10, 1987, now abandoned.

BACKGROUND OF THE INVENTION

This invention relates to genetically engineered DNA enabling organisms, particularly bacteria, to produce, process, and secrete desired mature proteins, particularly chitinase. The invention also relates to the use of such microorganisms for controlling pests that are sensitive to chitinase. The term "engineered" or "engineered DNA" means a DNA that has been modified by human intervention, e.g. by genetic engineering techniques.

Various organisms actively secrete enzymes that digest chitin, a complex carbohydrate found in insect cuticles and shellfish shells, comprising a polymer of N-acetylglucosamine monomer units. Chitinase has been proposed for use in a variety of applications, for example as a pesticide to combat pests such as fungi, nematodes, and insects. Fuchs et al., *Applied and Environ. Microbiol.* 51(3):504–509 (1986) propose enzymatic digestion or deformation of the chitin component of pests such as insects, fungi, and nematodes, to control those pests. They propose to produce and deliver chitinase to the site of infestation by appropriate rhizoplane- or phyloplane-colonizing bacteria such as fluorescent Pseudomonads.

Chitinase also can be used to process industrial waste, e.g., shellfish shells.

Chitinase genes of *Serratia marcescens* have been cloned. For example, Fuchs et al., cited above, report that *S. marcescens* produces five unique chitinolytic proteins, with subunit molecular masses of 21, 36, 48, 52, and 57 kilodaltons. A gene producing one of these proteins (the 57 kilodalton protein) was cloned and expressed in *Escherichia coli* and in *Pseudomonas fluorescens*. Suslow and Jones EP 0157351 disclose cloning of two independent chitinase genes from *S. marcescens*. Jaworski et al. EP 0171381 disclose cloning a chitinase gene from *S. marcescens*, and expression of the gene from a strong constitutive promoter in *P. fluorescens* to inhibit nematode infection of soybeans.

SUMMARY OF THE INVENTION

One aspect of the invention generally features engineered DNA encoding a pre-protein which comprises a Streptomyces chitinase signal sequence and a desired mature protein; the engineered DNA preferably also includes information preceding the chitinase signal-sequence encoding DNA to regulate its expression. As used in this application, the term "Streptomyces bacteria" or "Streptomyces" includes any bacterial strain that is a member of the genus Streptomyces as classified in Buchanan et al., *The Shorter Bergey's Manual for Determinative Bacteriology* [Williams and Williams, 1982]. "Signal sequence" means an amino acid sequence in the pre-protein effecting transport across the cell membrane. Cleavage of the signal sequence results in release of the mature protein from the pre-protein.

The preferred signal sequence is a *Streptomyces plicatus* chitinase signal, e.g. the sequence encoded by the following 90bp DNA sequence (the deduced amino acid sequence is also shown):

```
ATG CGT ATC AGA CAC AAA GCC GCG GCA CTC GCA GCG
Met Arg Ile Arg His Lys Ala Ala Ala Leu Ala Ala

AAC CTG GCG CTT CCC CTC GCC GGC CTG GTC GGC CTC GCG AGC CCG GCC
Thr Leu Ala Leu Pro Leu Ala Gly Leu Val Gly Leu Ala Ser Pro Ala

CAG GCC
Gln Ala .
```

This signal is preceded by a ribosome binding site, a promoter positioned and oriented to effect transcription of the signal-encoding DNA, and appropriate regulatory DNA contained in the sequence to induce transcription in response to the presence of chitin (see FIG. 1b). A suitable promoter (e.g., the *Streptomyces fradiae aph* promoter or the naturally occurring chitinase promoter) is positioned and oriented in the engineered DNA to initiate transcription of the preprotein-encoding DNA.

Suitable mature proteins are generally those whose Production is simplified or improved by secretion into the extracellular medium. Genes encoding a large number of such proteins have been cloned (e.g., growth hormones, lymphokines, antigens for vaccines, tPA), and the Streptomyces chitinase signal will operate generally to effect secretion and cleavage, without regard to the nature of the mature protein. To produce the mature protein, the DNA (including the promoter, chitinase regulatory DNA, and the signal sequence-mature protein-encoding DNA) is included in a host bacterium (e.g. a bacterium of the genus Streptomyces), the bacterium is cultured in a medium, and the mature protein is recovered from the medium. Certain complex carbohydrates such as chitin can be used to induce expression of the engineered DNA sequence.

Preferably, the desired mature protein is or Streptomyces chitinase, e.g., *S. plicatus* endochitinase, in which case the invention features engineered DNA encoding the mature Streptomyces chitinase (with or without the chitinase signal encoding DNA). This aspect of the invention can be used in a method of controlling chitinase sensitive pests by including the engineered DNA in a host organism (e.g., a bacterium of the genus Bacillus, Pseudomonas, Streptomyces, or Rhizobium) and administering the host to the site of the pests, e.g., in the rhizosphere of a crop plant desired to be protected. Alternatively, for plant pests, the engineered DNA can be transformed directly into plant cells.

Other features and advantages of the invention will be apparent from the claims and from the following description of preferred embodiments of the invention.

DESCRIPTION OF THE PREFERRED EMBODIMENTS

We first briefly describe the drawings of preferred embodiments of the invention.

FIG. 1a shows the nucleotide sequence of the junction region between pUC18 and the resected chitinase gene of pCTFI. The inferred amino acid sequence is also shown. The chitinase signal is shown by a thin line and the 5' end of DNA encoding the mature chitinase protein is shown by a heavier bold line.

FIG. 1b shows the nucleotide sequence of most of the cloned chitinase regulatory region on plasmid pCT4. The 5' nucleotide sequence, the inferred amino acid sequence of the signal sequence, and the 5' portion of the gene are also shown.

FIG. 3 is the flow diagram depicting construction of plasmids pOW1, pOW2 and pOW3 for the expression of chitinase in *S. lividans*.

FIG. 4 is the flow diagram depicting the construction of pPR5.

FIG. 6 shows the nucleotide sequence of a mutagenized region for introduction into a plasmid to create restriction sites between the signal sequence and the chitinase structural gene.

The features of the invention summarized above are illustrated by the following specific examples which detail: A) Cloning and expression of the *S. plicatus* endochitinase gene in *E. coli*; B) Expression of that gene is *S. lividans*; C) Production of chitinase; D) Properties of cloned chitinase; E) Engineering the chitinase gene; F) Isolation of other Streptomyces chitinases; G) Construction of vectors for secreting heterologous mature proteins; and H) Controlling Pests.

A. Cloning and Expression of the Chitinase Gene in *E. coli*

The bacteriophage lambda cloning vector EMBL4 (purchased from Promega Biotec) was used to make a DNA library from *S. plicatus*. The recommended Promega procedures were used for restriction enzyme digestion of the vector and ligation of DNA with phage arms. *S. plicatus* DNA was digested with Sau3A, size-selected on a sucrose gradient, and the 10–20 kb fraction was treated with calf-intestine alkaline phosphatase and then ligated with phage that had been digested with BamHI and EcoRI. Ligation of 1 μg of phage arms with 0.6μg of *S. plicatus* DNA gave a total yield to about $6 \times 10^6$ recombinant plaques following packaging and infection of *E. coli* NM538. Plaques were purified and phage DNA was isolated by standard procedures.

4-methylumbelliferyl glycosides of N-acetylglucosamine oligosaccharides (obtained from Sigma, St. Louis) were used as substrates to detect expression of Streptomyces chitinase in *E. coli* (See *Properties of Cloned Chitinase*, below). To screen for chitinase activity, the primary EMBL4 library was plated on 150 mm LB plates with 4-methylumbelliferyl substrate in the soft agar overlay (12.5 μg/ml of the trisaccharide or 25 μg/ml disaccharide), and were observed under long wavelength ultraviolet light as soon as the plaques began to form. Although the signal was extremely weak, faint fluorescent halos indicative of chitinase activity were observed around six of the $5 \times 10^5$ to $10^6$ plaques. Most positive plaques were detected after overnight incubation at 30° C.

Some positive clones were detected with the disaccharide substrate and others with the trisaccharide derivatives. Restriction mapping of the insert DNA suggested that the same enzyme was being expressed in all cases. All six inserts were in perfect register at one end.

Figure 2:
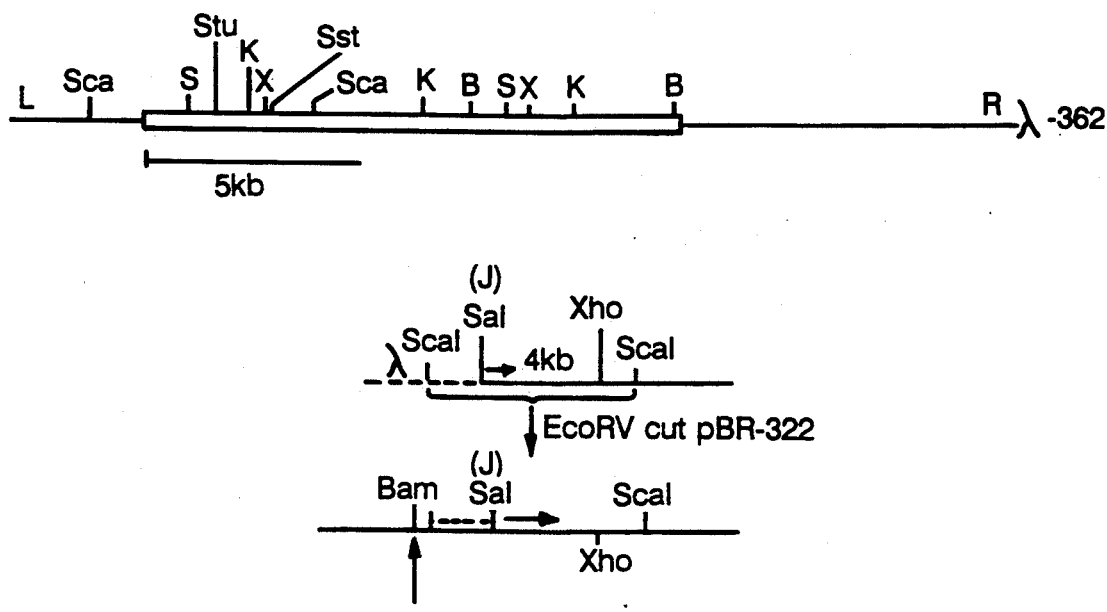
FIG. 2 is the flow diagram depicting the construction of plasmids pCTF1 and pCT4 for expression of chitinase in *E. coli*.

Subcloning confirmed that the 5' terminus of the gene in question was located near the common junction site with the vector DNA (the Sau3A site). Ligation of one end of the lambda insert into the EcoRV site of pBR322 gave low but detectable levels of enzyme (FIG. 2).

Bal-31 resection followed by a second subcloning into pUC-18 gave the following results. Plasmids with incomplete removal of the lambda DNA gave moderate levels of enzyme expression. Plasmids with the resection 150–200 bp into the insert gave rise in some cases to much higher levels of expression. Plasmids with resections of more than 200 bp in the insert led to complete inactivation.

These results suggest that, ordinarily, expression in *E. coli* is not very efficient, but that higher level expression was the result of fusion of the chitinase gene with the short β-galactosidase sequence of the pUC vector. One of these expression plasmids, pCTF1, was chosen for detailed analysis.

FIG. 1a shows the DNA sequence of the junction region between pUC18 and the resected chitinase gene of pCTF1. The sequence clearly suggests that DNA residues 7–9 code for the ATG start codon of the chitinase gene which in this case is fused in frame to the pUC β-galactosidase sequence. The first 30 amino acids of the chitinase gene are typical of the signal sequences found in secreted proteins of Gram-positive bacteria. Amino-terminal amino acid analysis of the chitinase protein purified from periplasmic extracts of *E. coli* carrying plasmid pCTF1 gave a sequence of 15 amino acids corresponding exactly with the sequence deduced starting at protein residue 31. This result confirms the location and orientation of the chitinase gene and shows that the *E. coli* signal peptidase cleaves the protein cleanly between two alanine residues, amino acids 30 and 31.

B. Expression of the Chitinase Gene in *S. lividans*

Since the chitinase gene in pCTF1 contained only 6 bp upstream of the ATG start sequence, we chose another of the above-described Bal31-resected expression plasmids, pCT4, for expression in Streptomyces. This construction contains about 150 bp of upstream DNA, enough to code for the ribosome binding site and at least some of the upstream control sequences. A low-copy number vector (pIJ61 ~10 copies/cell) and a high-copy number vector (pSEH, a derivative of pIJ702, ~100–300 copies/cell) were chosen for expression of the chitinase gene in *S. lividans*. pIJ61 and pIJ702 are well known Streptomyces vectors. (Thompson et al. *Gene* 20:51-62 (1982) and Hopwood, *J. Gen. Micro.* 129:2703-2714 (1983).)

For the low-copy number construct, the BamHI-XhoI fragment from pCTF4 was cloned between the BamHI and XhoI sites of pIJ61, directly downstream from the strong aph promoter. This plasmid is called pOW3 (FIG. 3).

Two methods were chosen for cloning into the high-copy vector pSEH. These two different cloning schemes allowed for insertion of the chitinase gene in two different orientations in pSEH. In the first, a BamHI to SacI fragment from pCT4 containing the chitinase gene was ligated into the BglII/SacI-cut backbone of pSEH, creating pOW1. In the second strategy, a BamHI to Asp718 fragment from pCT4 containing the chitinase gene was ligated into the BglII and Asp718 sites of the backbone pSEH, creating pOW2 (FIG. 3).

The three different plasmid constructions on high (pOW1, pOW2) and low-copy (pOW3) vectors were transformed into protoplasts of *S. lividans* as described in *Genetic Manipulation of Streptomyces, A Laboratory Manual*, Hopwood et al. The John Innes Foundation (1985) and all three plasmid constructions were capable of directing chitinase expression in the preliminary screen of transformants. Expression of the chitinase gene on the low-copy vector, pOW3, appeared to produce the most enzyme, as evidenced by a large clearing of chitin from the agar around these clones, compared to the significantly smaller clearing zones around clones bearing the chitinase gene on the high-copy vectors pOW1 and pOW2.

To quantitate these results, production of chitinase in liquid media by these strains was examined. Shake-flask fermentations were done in a minimal medium (glucose and $[NH_4]_2SO_4$ as the carbon and nitrogen source), in a minimal induction medium (chitin as both the carbon and nitrogen source), and a rich medium (containing glucose, maltose, peptone and yeast extract). The fermentations in liquid media were harvested on days 2, 4 and 6, and culture supernatants were examined for the presence of chitinase by a fluorometric assay.

The liquid fermentations with Streptomyces strains bearing pOW3 produced the most chitinase. The chitinase gene cloned onto the high-copy vector in two different orientations (pOW1 and pOW2) produced less chitinase than pOW3.

For both the chitinase gene on the low-copy vector and the high-copy vector there was a strong induction of chitinase production by inclusion of chitin in the minimal media. These results demonstrate the presence of a regulatory region necessary for induction of chitinase within the cloned fragment The regulatory region is contained within the roughly 150 bases of nucleotide sequence preceding the initiation codon of the signal sequence of the chitinase gene cloned on pCT4, as shown in FIG. 1b.

Fermentations demonstrate the presence of an inducible chitinase gene that upon induction results in high production of the cloned chitinase enzyme. SDS-polyacrylamide gel analysis and protein determinations indicate that the chitinase enzyme constitutes 80-90% of all protein in the culture medium in Streptomyces fermentations with pOW3.

C. Production of Chitinase

To produce chitinase, a suitable host, e.g. an *S. liyidans* strain, bearing the appropriate plasmid is grown in an appropriate medium at 30° C. with aeration. The plasmids described above are suitable. Other plasmids also can be used, for example, a strong promoter (e.g., aph) can be placed in the vector in a suitable position and orientation to enhance chitinase production.

For example, a minimal induction medium can be used with the following constituents per liter: 0.5 g KCl, 0.25 g $K_2HPO_4$, 0.5 g $MgSO_4$: $7H_2O$, 0.01 g $FeSO_4$, 10 g chitin, and Tris buffer 50mM at pH7.6.

A suitable rich broth medium is YEME broth having the following constituents per liter; 3 g Difco yeast extract, 5 g Difco peptone, 3 g Oxoid malt extract, 10 g glucose, 340 g sucrose and 5 mM MgC12.

The protein of interest is translated and secreted in substantial quantities, permitting efficient recovery and purification from the extracellular growth medium. Samples of culture are taken at various time points, centrifuged, and supernatant fractions assayed for the product. For example, chitinase may be quantitated by a fluorometric assay as described in Section D, below. Alkaline phosphatase may be assayed by the production of yellow color as described by Brickman and Beckwith (1975) *J. Mol. Biol.* 96:1–10.

Crude preparations containing 80-90% chitinase can be prepared by concentration, filtration and lyophilization. Standard column chromatographic techniques can be used for the purification of the enzyme, for example hydroxyapatite and gel filtration.

D. Properties of the cloned chitinase

The chitinase described in this application, chitinase-56, is one of the enzymes of the *S. plicatus* chitinase complex. Chitinase-56 is classified as an endochitinase by its cleavage properties of the 4-umbelliferyl oligosaccharides.

In detail, enzymes were assayed routinely by adding a 2-50 $\mu$l enzyme sample, diluted if necessary in solution A, to 2 ml of the 4-methylumbelliferyl trisaccharide or disaccharide (10$\mu$M) in solution A. The rate of appearance of fluorescence was observed directly (350nm excitation, 440nm emission) in a Perkin-Elmer model 650-15 spectrofluorometer. Although these conditions were not optimal for enzymatic reaction rate or for detection of fluorescence, they were used for convenience and for the accuracy inherent in direct rate measurements. For measurements of pH optimum and for other purposes, incubations were carried out in a final volume of 100$\mu$l and were quenched by dilution to a final volume of 2 ml with 0.1M glycine pH10.4 before fluorescence measurement. The fluorescence of 4-methylumbelliferone in solution A is 38% of that in 0.1M glycine pH10.4. Chitinase 56 produces 4-methylumbelliferone more rapidly from the trisaccharide than from the disaccharide derivative. This enzyme forms more 4-methylumbelliferone than 4-methylumbelliferone monosaccharide (a non-fluorescent product) from both a 4-methylumbelliferone trisaccharide and tetrasaccharide, and thus has been classified here as an endochitinase.

Preliminary experiments indicate that the chitinase hydrolyzes radioactive chitin most rapidly at pH 6, and has approximately half-maximal rate for this reaction at pH 4.5 and 7.5.

Preliminary experiments also indicate that chitinase is a very stable enzyme. No loss of enzyme activity was found after the following treatments: freezing and thawing, storage for 6 days at 4° C., heating to 65° C., or lyophilization and reconstitution.

E. Engineering the chitinase gene

Plasmids can be constructed by oligo-directed mutagenesis to contain unique restriction sites (BamHI and PstI) between the signal sequence and structural gene of chitinase (See FIG. 6). These sites are useful for heterologous promoter and signal sequence fusions to the Streptomyces chitinase structural gene. Such constructions will allow for expression, translation and secretion in other bacterial systems (e.g. Bacillus, *E. coli*, Pseudomonas, etc.), by insertion of the appropriate promoter and signal sequence using known techniques.

F. Isolation of Other Streptomyces Chitinases

The cloned chitinase-56 gene can be used as a tool for the isolation of other enzyme members of the Streptomyces chitinase complex. Using standard DNA hybridization techniques the DNA from the cloned chitinase-56 gene can be used as a radioactive probe for the identification of other structurally related chitinase genes from a library of Streptomyces DNA, such as the S. plicatus library described above.

G. Construction of Secretion Vectors for Heterologous Mature Proteins

Because chitinase is expressed and secreted from the above-described vectors at very high levels, it is possible to use the regulatory signals, primarily the induction signals, ribosome binding site, and the signal sequence, in a secretion vector for generalized protein secretion in Streptomyces. As shown in FIG. 1, the first 30 amino acids of the protein sequence, encoded by the first 90 bp of the gene, correspond to a typical Gram-positive signal peptide. The preferred cleavage site is believed to be between $Ala_{30}$ and $Ala_{31}$, although it is possible that in some hosts cleavage may occur in a different location.

Three different approaches can be taken to use the cloned chitinase gene, signal sequence, and/or regulatory region for the construction of new secretion vectors.

In one approach a vector in which the gene for bacterial alkaline phosphatase is placed under the control of the chitinase regulatory sequences was constructed. The vector PPR5 was constructed in a two step series of constructions as diagrammed in FIG. 4. In the first series of constructions, the pCT4 plasmid was digested with BamHI and SacI. The fragment bearing the chitinase gene was ligated into BamHI SacI cut pUC19 creating plasmid pCB5. The phoA fragment came from a PstI digestion of plasmid pCH39 (ref. Hoffman and Wright, PNAS 5107-5111 (1985)). The phoA PstI fragment was ligated into PstI cut pUC8 creating pNH214. In the second series of constructions pCB5 was partially digested with EaeI, the fragments blunt-ended with Klenow, and the blunt-end ligated into SmaI cut pNH214. Plasmid pPR5 contains@250 bp of Streptomyces DNA. The pPR5 vector enables the expression and secretion of alkaline phosphatase in E. coli.

Figure 5A:
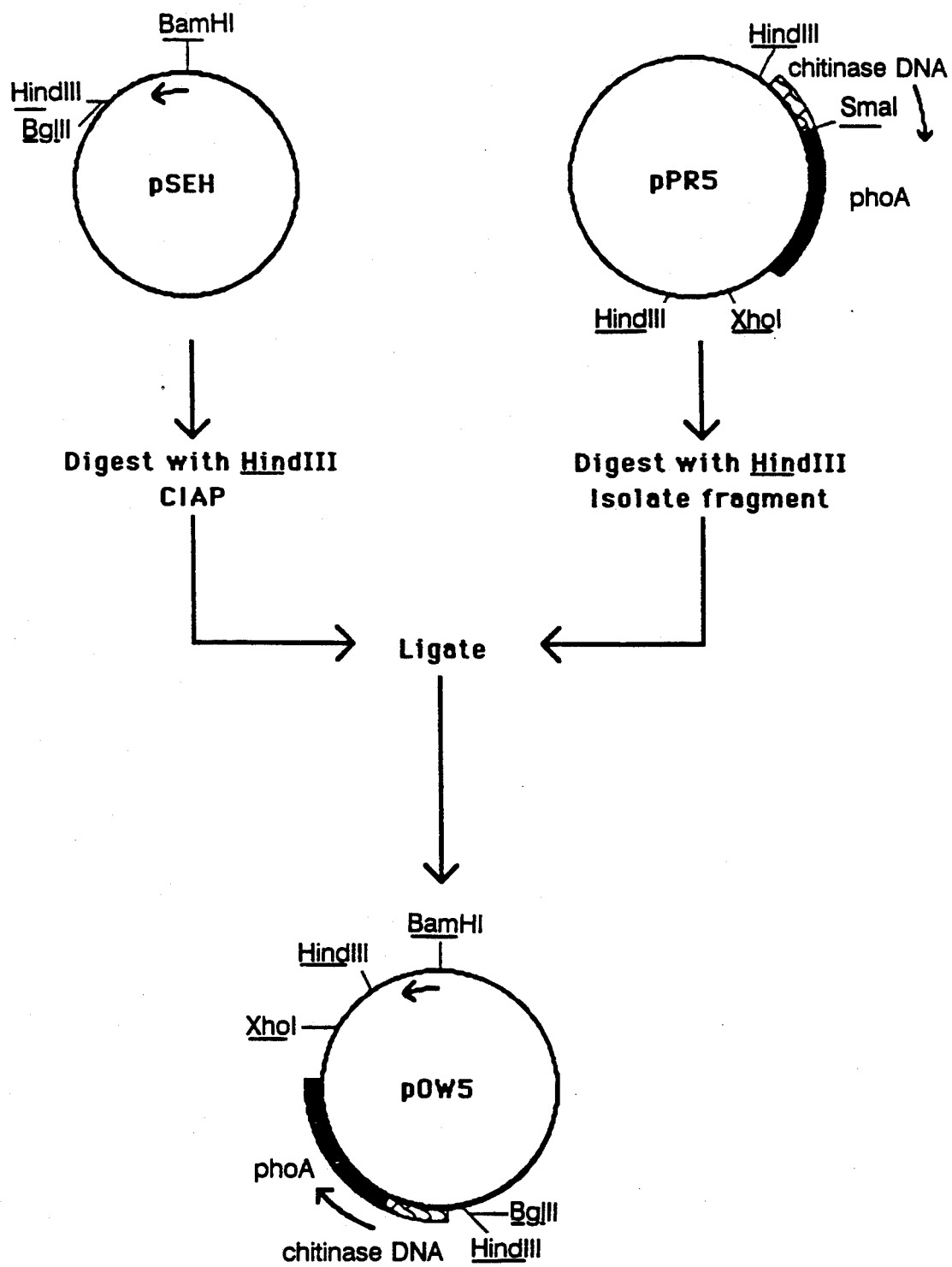
FIGS. 5A and 5B are flow diagrams depicting the construction of pOW5, and a strategy for constructing a secretion vector analogous to pOW3.
Figure 5B:
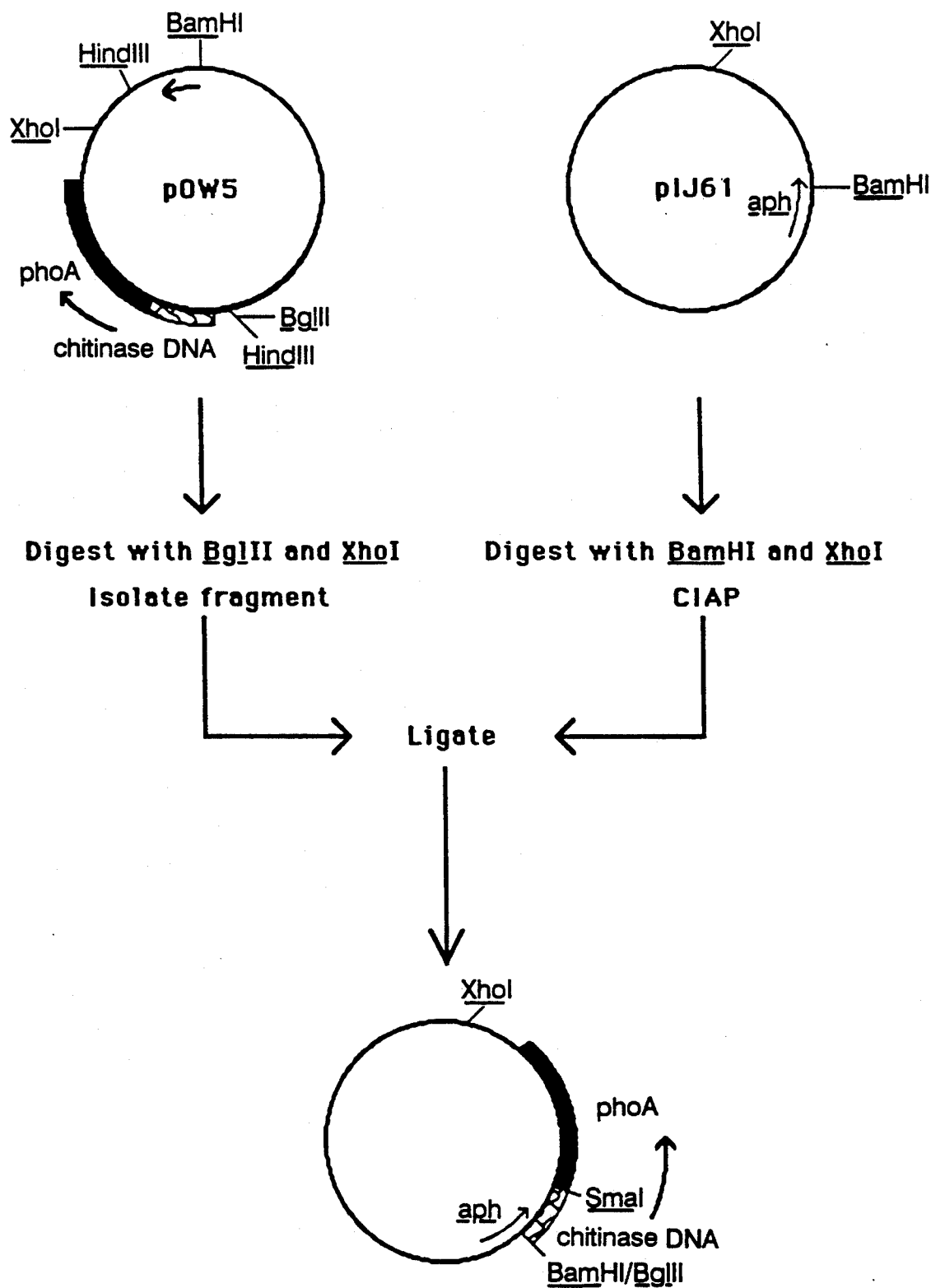

For the expression and secretion of E. coli alkaline phosphatase in Streptomyces, the 3.2 kb HindIII fragment of pPR5 carrying the chitinase-phoA fusion was ligated into the HindIII site of pSEH. Plasmids were recovered where the fusion was inserted in the orientation shown in FIG. 5. The appropriate BqlII-XhoI fragment can than be isolated and ligated into the BamHI-XhoI sites of pIJ61.

Other structural genes for other commercially useful proteins (i.e. growth hormones, lymphokines, vaccines, tPA, etc.) may be inserted in place of the E. coli alkaline phosphatase gene described above.

Another approach for the design of a secretion vector utilizes oligo-directed mutagenesis for the insertion of cloning sites (BamHI and PstI) between the signal sequence and the structural gene of chitinase (see FIG. 6). These cloning sites allow the insertion of other structural genes in place of the chitinase structural gene by known techniques. The resulting vectors are then transformed into a suitable host. The host is then cultured by known suitable techniques and the product is recovered. The new protein of interest will be translated and secreted by Streptomyces using the chitinase signal sequence. Expression and secretion of the protein will also be regulated by the upstream chitinase DNA regulatory sequences.

In a third approach, a desired structural gene is inserted within the chitinase gene or at its 3' end, using an appropriate restriction site, so that the desired gene is in the same reading frame as the chitinase gene. When the resulting vectors are transformed into a suitable host, and the host is cultured by known suitable techniques, a fusion protein will be translated and secreted by Streptomyces, consisting of all or part of the chitinase protein and the protein or peptide encoded by the desired structural gene. The desired protein or peptide may then be cleaved from the chitinase protein by standard methods. This approach for secretion may be particularly useful for expression and secretion of small peptides, which may be protected from proteolytic digestion by fusion to the chitinase protein.

H. Controlling Pests

Chitinase produced as described above may be administered directly (e.g., in solution or as a finely divided solid mixed with inert material) to the site of pests, e.g. sites of fungal, nematade or insect infestation. The resulting method of pest control avoids toxic chemicals.

Alternatively, the chitinase gene is transformed into a host as described in the above-cited European Patent Applications and the host is administered to the pest site, e.g., a plant. Also, when the pest is a plant pest, the chitinase gene can be transformed directly into the plant cells, and the plant cells regenerated into whole plants.

Deposits

The following deposits of plasmids described above have been made with the American Type Culture Collection, Rockville, MD:

| Deposit | ATCC No. |
| --- | --- |
| pOW3 in S. lividans 1326 | 67333 |
| pPR5 in E. coli JM107 | 67332 |

Applicants' assignee, BioTechnica International, Inc., requests that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

OTHER EMBODIMENTS

Other embodiments are within the following claims. For example, other structural genes encoding other desired mature proteins can be inserted in the above vectors, or other vectors comprising the chitinase signal encoding DNA.

We claim:

1. An isolated recombinant DNA sequence comprising a transcription unit encoding a preprotein, said transcription unit comprising DNA encoding a *Streptomyces plicatus* endochitinase 56 signal peptide, attached to the 5' end of a structural gene.

2. The isolated recombinant DNA sequence of claim 1, wherein said DNA sequence comprises a regulatory DNA unit, said regulatory DNA unit consisting essentially of a sequence of about 150 base pairs from a segment of the plasmid pPR5 (ATCC 67323) immediately upstream from *Streptomyces plicatus* endochitinase 56 signal peptide-encoding DNA on said plasmid, said regulatory DNA unit being positioned upstream of said transcription unit to effect regulated transcription of said transcription unit.

3. The isolated recombinant DNA sequence of claim 2, wherein said regulatory DNA unit effects transcription of said preprotein encoding DNA in response to the presence of chitin.

4. The isolated recombinant DNA sequence of claim 1, wherein said DNA sequence encodes a signal sequence comprising: Met Arg Ile Arg His Lys Ala Ala Ala Leu Ala Ala Thr Leu Ala Leu Pro leu Ala Gly Leu Val Gly LEu Ala Ser Pro Ala Gln Ala.

5. The isolated recombinant DNA sequence of claim 4 comprising the sequence: ATG CGT ATC AGA CAC AAA GCC GCG GCA CTC GCA GCG ACC CTG GCG CTT CCC CTC GCC GGC CTG GTC GGC CTC GCG AGC CCG GCC CAG GCG.

6. The isolated recombinant DNA sequence of claim 1, wherein said preprotein comprises a chitinase.

7. The isolated recombinant DNA sequence of claim 1, wherein said DNA sequence is contained on a plasmid selected from the group consisting of pCTF1, pCT4, pOW1, pOW2, pOW3, and pOW5.

8. The isolated recombinant DNA sequence of claim 1, wherein said DNA sequence comprises the *Streptomyces fradiae* aph promoter positioned and oriented to transcribe said preprotein-encoding DNA.

9. A Streptomyces bacterium containing the isolated recombinant DNA sequence of claim 1.

10. An isolated recombinant DNA sequence encoding a functional Streptomyces endochitinase, said DNA sequence comprising the *Streptomyces plicatus* endochitinase 56 structural gene.

11. The isolated recombinant DNA sequence of claim 10 wherein said *Streptomyces plicatus* endochitinase 56 structural gene is *Streptomyces plicatus* endochitinase 56-encoding DNA sequence of ATCC 67332 or ATCC 67333.

12. A microorganism comprising the isolated recombinant DNA sequence of claim 10, wherein said microorganism is a bacterium.

13. The microorganism of claim 12, wherein said microorganism is a bacterium of the genus Streptomyces, Pseudomonas, Bacillus, Escherichia, or Rhizobium.

14. An isolated recombinant DNA expression vector comprising a gene to be expressed and regulatory DNA from the DNA sequence consisting essentially of about 150 base pairs upstream from the signal peptide-encoding DNA sequence of the *Streptomyces plicatus* endochitinase 56 gene, said regulatory DNA being operationally linked upstream from the 5' end of said gene to be expressed.

15. An isolated recombinant DNA sequence comprising the DNA sequence

| TAGTTTTCCC | TAGTCAGTCA | CAGGTTCAAC | CACTGGCCGC | CACATTGGTC | CAGACCTATT |
| GACCTGTGGT | CCAGACCTTT | CTATTCTCGC | CGCACTGCGG | GCATGAGGCT | CAGTCATGCC |
| CTCGACAACA | TCCCCATAAA | AGGAGGCGCA | CATGCGTATC | AGACACAAAG | CCGCGGCACT |
| CGCAGCGACC | CTGGCGCTTC | CCCTCGCCGG | CCTGGTCGGC | CTCGCGAGCC | CGGCCCAGGC |
| GGCCACCAGC | GCGACGGCCA | CCTTCCAGAA | GACCTCGGAC | TGG | |

* * * * *